United States Patent [19]

Quadri et al.

[11] Patent Number: 5,567,697
[45] Date of Patent: Oct. 22, 1996

[54] 17-(4-PYRIDAZINYL) -5β, 14β-ANDROSTANE DERIVATIVES ACTIVE ON THE CARDIOVASCULAR SYSTEM, PROCESSES FOR THEIR PREPARATION AND PHARMACEUTICAL COMPOSITIONS CONTAINING SAME

[75] Inventors: Luisa Quadri, Cernusco; Luigi Bernardi; Giuseppe Bianchi, both of Milan; Patrizia Ferrari, Varese; Piero Melloni, Bresso; Loredana Valentino, Buccinasco, all of Italy

[73] Assignee: Sigma-Tau Industrie Farmaceutiche Riunite S.p.A., Rome, Italy

[21] Appl. No.: 458,822

[22] Filed: Jun. 2, 1995

Related U.S. Application Data

[62] Division of Ser. No. 106,893, Aug. 16, 1993.

[30] Foreign Application Priority Data

Aug. 20, 1992 [DE] Germany ............. 42 27 616.0

[51] Int. Cl.$^6$ .............. A61K 31/58; C07J 71/00
[52] U.S. Cl. .............. 514/176; 540/83; 540/95
[58] Field of Search ............ 540/83, 95; 514/176

[56] References Cited

U.S. PATENT DOCUMENTS 5,432,169  7/1995  Quadri et al. .

*Primary Examiner*—Mukund J. Shah
*Assistant Examiner*—Anthony Bottino
*Attorney, Agent, or Firm*—Oblon, Spivak, McClelland, Maier & Neustadt, P.C.

[57] ABSTRACT

Present invention relates to a group of 17-(4-pyridazinyl)-5β,14β-androstane derivates active on the cardiovascular system and to pharmaceutical compositions containing same.

7 Claims, No Drawings

17-(4-PYRIDAZINYL) -5β, 14β-ANDROSTANE DERIVATIVES ACTIVE ON THE CARDIOVASCULAR SYSTEM, PROCESSES FOR THEIR PREPARATION AND PHARMACEUTICAL COMPOSITIONS CONTAINING SAME

This is a Division of application Ser. No. 08/106,893, filed on Aug. 16, 1993, pending.

The present invention relates to a group of 17-(3-furyl) and (4-pyridazinyl)-5β,14β-androstane derivatives, active on the cardiovascular system, to processes for their preparation and to pharmaceutical compositions containing same for the treatment of cardiovascular disorders such as heart failure and hypertension.

More specifically the invention relates to compounds of formula (I):

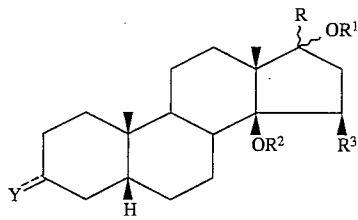

wherein:
the symbol ⁓ means that the substituents in position 17 can have an α or β configuration:
the symbol --- represents a single or a double bond:
Y is oxygen or guanidinoimino, when --- in position 3 is a double bond:
Y is hydroxy, $OR^4$ or $SR^4$, when --- in position 3 is a single bond and can have an α or β configuration:
R is an unsubstituted or substituted 3-furyl or 4-pyridazinyl group:
$R^1$ is hydrogen: methyl; ethyl or n-propyl substituted by OH or $NR^5R^6$;
$R^2$ is hydrogen or together to $R^3$ is a bond of an oxirane ring;
$R^3$ is hydrogen or together to $R^2$ is a bond of an oxirane ring;
$R^4$ is hydrogen: methyl; C2–C6 alkyl or C3–C6 alkenyl or C2–C6 acyl, these alkyl, alkenyl and acyl groups being unsubstituted or substituted by a quaternary ammonium group or one or more $OR^7$, $NR^8R^9$, formyl, amidmo, guanidinoimino or by $NR^8R^9$ and hydroxy;
$R^5$, $R^6$ are independently hydrogen; methyl; C2–C6 alkyl unsubstituted or substituted by one $NR^{10}R^{11}$, or $NR^{10}R^{11}$ and hydroxy, or $R^5$ and $R^6$ taken together with the nitrogen atom form an unsubstituted or substituted saturated or unsaturated penta- or hexa-monoheterocyclic ring, optionally containing another heteroatom chosen from oxygen or sulfur or nitrogen;
$R^7$ is hydrogen, methyl or C2–C4 alkyl, this alkyl being unsubstituted or substituted by one or more $NR^{10}R^{11}$ or by $NR^{10}R^{11}$ and hydroxy;
$R^8$, $R^9$ are independently hydrogen: methyl: C2–C6 alkyl or C3–C6 alkenyl, these alkyl and alkenyl groups being unsubstituted or substituted by one or more $NR^{10}R^{11}$, or $NR^{10}R^{11}$ and hydroxy, or $R^8$ and $R^9$ taken together with the nitrogen atom form an unsubstituted or substituted saturated or unsaturated penta- or hexa-monoheterocyclic ring, optionally containing another heteroatom chosen from oxygen or sulfur or nitrogen, or $R^8$ is hydrogen and $R^9$ is amidino;
$R^{10}$, $R^{11}$ are independently hydrogen, C1–C6 alkyl, or $R^{10}$ and $R^{11}$, taken together with the nitrogen atom form a saturated or unsaturated penta- or hexa-monoheterocyclic ring.

The invention includes within its scope all the possible stereoisomers, in particular Z and E isomers, optical isomers and their mixtures and the metabolites and the metabolic precursors of the compounds of formula (I).

Also included in this invention are pharmaceutically acceptable salts of (I), which retain the biological activity of the base and are derived from such known pharmaceutically acceptable acids such as hydrochloric, sulfuric, phosphoric, malic, tartaric, maleic, citric, methanesulfonic or benzoic acid.

The alkyl and alkenyl groups may be branched or straight chain groups.

The C1–C6 alkyl group is preferably a C1–C4 alkyl group, e.g. methl, ethyl, n-propyl, isopropyl, n-butyl, sec-butyl.

The C2–C6 alkyl group is preferably a C2–C4 alkyl group, e.g. ethyl, n-propyl, isopropyl, n-butyl, sec-butyl.

The C3–C6 alkenyl group is preferably a C3–C4 alkenyl group, e.g. 2-propenyl, 2-butenyl.

The C2–C6 acyl is preferably a C2–C4 acyl group, e.g. acetyl, propionyl, butyryl.

The quaternary ammonium group is preferably a trimethylammonium- or a N-methylpyrrolidinium- or a N-methylpiperidinium-group.

The $OR^7$ group is preferably hydroxy, 2-aminoethoxy, 3-aminopropoxy, 2-dimethylaminoethoxy, 2-diethylaminoethoxy, 3-dimethylaminopropoxy, 3-amino-2-hydroxypropoxy, 2,3-diaminopropoxy, 2-(1-pyrrolidinyl)ethoxy, 3-(1-pyrrolidinyl)propoxy.

The $NR^5R^6$ group is preferably amino, methylamino, ethylamino, n-propylamino, dimethylamino, diethylamino, pyrrolidinyl, morpholino, piperazinyl, 1-imidazolyl, 2-aminoethylamino, 3-aminopropylamino.

The $NR^8R^9$ group is preferably amino, methylamino, ethylamino, n-propylamino, iso-propylamino, allylamino, propargylamino, dimethylamino, diethylamino, pyrrolidinyl, morpholino, piperazinyl, 1-imidazolyl, 1-guanidino, 2-aminoethylamino, 3-aminopropylamino, 2-(1-pyrrolidinyl)ethylamino, 3-(1-pyrrolidinyl)propylamino, 3-amino-2-hydroxypropylamino, 3-(1-pyrrolidinyl)2-hydroxypropylamino, 2,3-diaminopropylamino, (2-(1-pyrrolidinyl)ethyl)methylamino.

Preferred examples of specific compounds according to the present invention are
17β-(3-Furyl)-5β-androstane-3β, 14β,17α-triol
3β-(2-Hydroxyethoxy)-17β-(3-furyl)-5β-androstane-14β, 17α-diol
3β-(2-Aminoethoxy)-17β-(3-furyl)-5β-androstane-14β, 17α-diol
3β-(3-Aminopropoxy)-17β-(3-furyl)-5β-androstane-14β, 17α-diol
3β-(2-Methylaminoethoxy)-17β-(3-furyl)-5β-androstane-14β,17α-diol
3β-(2-(1-Pyrrolidinyl)ethoxy)-17β-(3-furyl)-5β-androstane-14β,17α-diol
3β-(2-(3-(1-Pyrrolidinyl)propoxy)ethoxy)-17β-(3-furyl)-5β-androstane-14β,17α-diol
3β-(3-(1-Pyrrolidinyl)propoxy)-17β-(3-furyl)-5β-androstane-14β,17α-diol
3β-(2-(1-Imidazolyl)ethoxy)-17β-(3-furyl)-5β-androstane-14β, 17α-diol
3β-(2-(2-Imidazolin-2-yl)ethoxy)-17β-(3-furyl)-5β-androstane-14β,17α-diol
3β-(2-(2-Amidino)ethoxy)-17β-(3-furyl)-5β-androstane-14β, 17α-diol 3β-(2-(2-(1-Pyrrolidinyl)ethoxy)ethoxy)-17β-(3-furyl)-5β-androstane-14β,17α-diol
3β-(2-Guanidinoethoxy)-17β-(3-furyl)-5β-androstane-14β,17α-diol
3β-(3-Guanidinopropoxy)-17β-(3-furyl)-5β-androstane-14β,17α-diol
3β-(3-Amino-2-hydroxypropoxy)-17β-(3-furyl)-5β-androstane-14β,17α-diol
3β-(2,3-Diaminopropoxy)-17β-(3-furyl)-5β-androstane-14β,17α-diol
17β-(3-Furyl)-17α-methoxy-5β-androstane-3β,14β-diol
17β-(3-Furyl)-17α-(2-(1-pyrrolidinyl)ethoxy)-5β-androstane-3β,14β-diol
17β-(3-Furyl)-17α-(3-aminopropoxy)-5β-androstane-3β,14β-diol
3β-(2-(1-Pyrrolidinyl)ethoxy)-17β-(3-furyl)-17α-methoxy-5β-androstan-14β-ol
3β,17α-Bis(2-(1-pyrrolidinyl)ethoxy)-17β-(3-furyl)-5β-androstan-14β-ol
3β,17α-Bis(3-aminopropoxy)-17β-(3-furyl)-5β-androstan-14β-ol
14β,17α-Dihydroxy-17β-(3-furyl)-5β-androstan-3-one
3-Guanidinoimino-17β-(3-furyl)-5β-androstane-14β,17α-diol
17β-(4-Pyridazinyl)-5β-androstane-3β,14β,17α-triol
3β-(2-Hydroxyethoxy)-17β-(4-pyridazinyl)-5β-androstane-14β,17α-diol
3β-(3-Aminopropoxy)-17β-(4-pyridazinyl)-5β-androstane-14β,17α-diol
3β-(2-(1-Pyrrolidinyl)ethoxy)-17β-(4-pyridazinyl)-5β-androstane-14β,17α-diol
3β-(3-(1-Pyrrolidinyl)propoxy)-17β-(4-pyridazinyl)-5β-androstane-14β,17α-diol
17β-(4-Pyridazinyl)-17α-(3-aminopropoxy)-5β-androstane-3β,14β-diol
3β-(2-(1-Pyrrolidinyl)ethoxy)-17β-(4-pyridazinyl)-17α-methoxy-5β-androstan-14 β-ol
3β-(2-(1-Pyrrolidinyl)ethoxy)-17β-(4-pyridazinyl)-17α-(3-aminopropoxy)-5β-androstan-14β-ol
14β,17α-Dihydroxy-17β-(4-pyridazinyl)-5β-androstan-3-one
3-Guanidinoimino-17β-(4-pyridazinyl)-5β-androstane-14β,17α-diol
14β,15β-Epoxy-17β-(3-furyl)-5β-androstane-3β,17α-diol
3β-(2-Hydroxyethoxy)-14β,15β-epoxy-17β-(3-furyl)-5β-androstan-17α-ol
3β-(3-Aminopropoxy)-14β,15β-epoxy-17β-(3-furyl)-5β-androstan-17α-ol
3β-(2-(1-Pyrrolidinyl)ethoxy)-14β,15β-epoxy-17β-(3-furyl)-5β-androstan-17 α-ol
3β-(3-(1-Pyrrolidinyl)propoxy)-14β,15β-epoxy-17β-(3-furyl)-5β-androstan-17 α-ol
3β-(2-(1-Pyrrolidinyl)ethoxy)-17β-(3-furyl)-17α-methoxy-14β,15β-epoxy-5β-androstane
17α-Hydroxy-17β-(3-furyl)-14β,15β-epoxy-5β-androstan-3-one
3-Guanidinoimino-17β-(3-furyl)-14β,15β-epoxy-5β-androstan-17α-ol
14β,15β-Epoxy-17β-(4-pyridazinyl)-5β-androstane-3β,17α-diol
17α-(3-Furyl)-5β-androstane-3β,14β,17β-triol
3β-(2-(1-Pyrrolidinyl)ethoxy)-17α-(3-furyl)-5β-androstane-14β,17β-diol
3β,17β-Bis(2-(1-pyrrolidinyl)ethoxy)-17α-(3-furyl)-5β-androstan-14β-ol
17α-(4-Pyridazinyl)-5β-androstane-3β,14β,17β-triol
3β-(2-(1-Pyrrolidinyl)ethoxy)-17α-(4-pyridazinyl)-5β-androstane-14β,17β-diol 3β,17β-Bis(2-(1-pyrrolidinyl)ethoxy)-17α-(4-pyridazinyl)-5β-androstan-14β-ol
and the 3α derivatives of the above identified 3β derivatives and also the corresponding 3α and 3β thioderivatives (Y=S).

The invention furthermore relates to a process for the preparation of compounds of general formula (I), which comprises the reduction with a complex metal hydride of compounds of general formula (II):

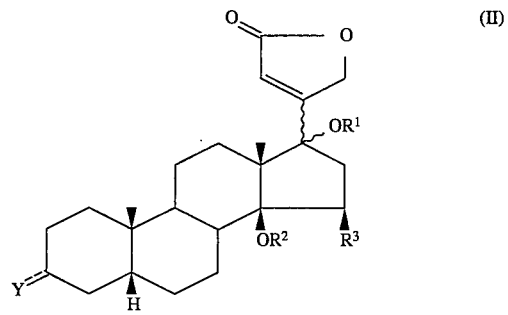

wherein $R^1$, $R^2$, $R^3$ and Y are as above defined except that Y is not a guanidinoimino and Y do not contain a guanidinoimino or a guanidino or an amidino group, the hydroxy, mercapto, amino and oxo groups, if any, present in Y, $R^1$ and/or $R^2$ being protected, if necessary, by known methods, to give, if necessary, after removal of the protective groups, if any, present in Y, $R^1$ and/or $R^2$, compounds of general formula (I), wich can be converted into other compounds of general formula (I) by known methods. These known methods comprise e.g. the conversion of hydroxy into mercapto function, the alkylation of hydroxy or mercapto groups, the oxydation of hydroxy or reduction of oxo functions, the formation of guanidinoimino or guanidino or amidino groups from oxo or primary amino or cyano groups respectively, or the reduction of a double bond to a single bond, as well as the conversion of a furyl ring into a pyridazinyl ring.

In particular, the compounds of general formula (I) wherein Y is 3α-or 3β-hydroxy, when --- in position 3 is a single bond, or oxygen, when --- in position 3 is a double bond, $R^1$ is hydrogen, $R^2$ is hydrogen, R is 3-furyl and $R^3$ is hydrogen, are obtained by reduction with complex hydrides, such as, e.g. diisobutylaluminum hydride, from the corresponding known 17-lactones (II), such as, e.g., 3β,14β,17α-trihydroxy-5β-card-20(22)-enolide (N. Danieli, et al., *Tetrah. Lett.*, 1962, 1281), 3-oxo-14β,17α-dihydroxy-5β-card-20(22)-enolide (M. L. Carvalhas, et al., *Drug Metab. Dispos.*, 1983, 11, 85), 3β,14β,17β-trihydroxy-5β,17α-card-20(22)-enolide (Saito, et al., *Chem. Pharm. Bull*, 1970, 18, 629), or from 17-lactones easily obtainable from (II) by methods well known by those skilled in the art.

The compounds of general formula (I) wherein Y is 3α- or 3β-hydroxy, when --- in position 3 is a single bond, or oxygen, when --- in position 3 is a double bond, $R^1$ is hydrogen, $R^2$ together to $R^3$ is a bond of an oxirane ring, R is 3-furyl, are obtained from the corresponding known 17β-lactones (III), such as, e.g. 3β-hydroxy-14β,15β-epoxy-5β-card-20 (22)-enolide (H. Ishii, et al., *Chem. Pharm. Bull.*, 1963, 11,576), 3α-hydroxy-14β,15β-epoxy-5β-card-20(22)-enolide (DE Pat. 1,807,585), 3β-hydroxy-14β,15β-epoxy-5β,17α-card-20(22)-enolide (Y. Saito, et al., *Chem. Pharm. Bull.*, 1971, 19, 1363), 3-oxo-14β,15β-epoxy-5β-card-20 (22)-enolide (DE Pat. 1,807,585), by oxidation with SeO₂ and subsequent reduction of the unsaturated lactone with complex hydrides, such as, e.g., diisobutylaluminum hydride.

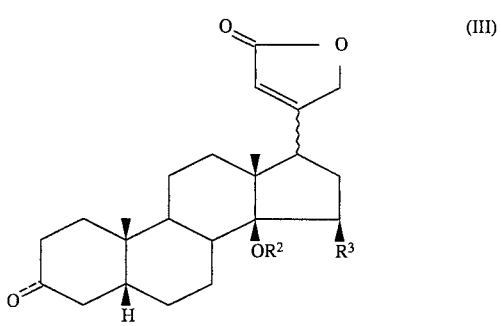

The reduction of a compounds of general formula (II) to a compound of general formula (I) is carried out with complex metal hydrides, such as e.g. NaBH₄, LiAlH₄ or lithium tri-tertbutoxyaluminum hydride, diisobutylaluminum hydride in an inert solvent such as methanol, ethanol, tetrahydrofuran, ethyl ether, dichlorometane, dioxane, hexane, cyclohexane or a mixture thereof, at a temperature ranging from −78° C. to the reflux temperature of the solvent mixture. The reaction time varies from a few minutes to several hours.

The compounds (I) wherein R is 4-pyridazinyl, and wherein Y, $R^1$, $R^2$ and $R^3$ are as above defined, except that Y is not a guanidinoimino and Y do not contain a guanidinoimino or a guanidino or an amidino group, are obtained from the corresponding compounds where R is 3-furyl with NBS/AcONa and hydrazyne hydrate with the amino and oxo groups optionally present in Y and/or $R^1$ protected, if necessary, by known methods, to give, if necessary, after removal of protective groups, if any, compounds of general formula (I), wich can be converted into other compounds of general formula (I) by known methods.

For example, the compounds (I), wherein Y is $OR^4$ or $SR^4$ and $R^1$, $R^2$ and $R^3$ are as above defined can be prepared from the corresponding compounds (I), wherein $R^1$ and/or $R^4$ are hydrogen and $R^2$ and $R^3$ are as above defined, by condensation with compounds of formula (IV), (V),

wherein $R^1$ and $R^4$ are as above defined except hydrogen and Z is an electron-withdrawing group, such as halogen, mesyloxy, or tosyloxy group, which confers electrophylic properties to the attached carbon atom. The reaction is carried out in an inert aprotic solvent, such as tetrahydrofuran, dioxane, dimethylformamide, dimethylsulfoxyde or in neat $R^1$-Z or $R^4$-Z in the presence of a base, such as, e.g. sodium or potassium hydride, at a temperature ranging from 0° C. to the reflux temperature of the reaction mixture.

The compounds of general formula (IV) and (V), are known compounds, generally commercially available or preparable from known compounds by known methods.

The compounds (I) wherein an oxo function is present can be obtained by oxidation of the corresponding compounds (I) with a hydroxy function with e.g. $CrO_3$ in pyridine or tetrapropylammonium perruthenate and N-methylmorpholine-N-oxide in methylene chloride, at temperature ranging from 0° C. to room temperature.

The compounds (I) wherein Y is an α-hydroxy group can be obtained by reduction of the corresponding compounds (I) wherein Y is oxygen with complex hydrides, e.g. NaBH₄, LiAlH₄ or lithium tri-tert-butoxyaluminum hydride in methanol, tetrahydrofuran or ethyl ether, at temperature ranging from −78° C. to room temperature.

The compounds (I) wherein a guanidinoimino group is present can be obtained by condensation of the corresponding compounds (I) wherein an oxo function is present with e.g. aminoguanidine hydrogencarbonate in ethanol, methanol, acetonitrile, dioxane or tetrahydrofuran, at temperature ranging from room temperature to the solvent reflux temperature.

The compounds (I) wherein Y is a β-mercapto group can be obtained by ammonolysis of the 3β-acetylthio derivatives (I) that are in turn obtained by reaction of the corresponding 3α-hydroxy derivatives (I) with e.g. thiolacetic acid in the presence of a dialkyl azodicarboxylate and triphenylphosphine, at temperature ranging from 0° C. to room temperature.

The compounds (I) wherein an amidino or a 2-imidazolinyl group are present can be obtained by reacting the corresponding compounds of formula (I) wherein a cyano group is present with e.g. methylchloroaluminum amide or 1,2-diaminoethane in the presence of hydrogen sulfide.

The compounds (I) wherein a guanidino group is present can be obtained by reacting the corresponding compounds of formula (I) wherein a primary amine is present with e.g. 1-amidino-3,5-dimethylpyrazole nitrate.

All said transformations are only examples of well established procedures described in Organic Chemistry (see for example: J. March "Advanced Organic Chemistry", J. Wiley & Sons. 1985; D. Barton and W. D. Ollis "Comprehensive Organic Chemistry", Pergamon Press, 1979) well known to those skilled in the art.

The compound 3β,14β,17α-trihydroxy-5β-card-20(22)-enolide (Ref. comp.) is known (N. Danieli, et al., *Tetrah. Lett.*, 1962, 1281); this compound and its congeners are described as agents against cardiac insufficiency (DT Pat. 2614-046; F. G. Henderson and K. K. Chen, *J. Med. Chem.*, 1965, 577), but do not show antihypertensive action.

We have found that the derivatives (I), prepared according to the invention, and their pharmaceutically acceptable salts have much reduced toxicity compared to the known 3β,14β,17α-trihydroxy-5β-card-20(22)-enolide and are useful agents for the treatment of cardiovascular disorders, such as heart failure and hypertension. Moreover said compounds (I) show affinity for the receptor site of the $Na^+,K^+$-ATPase and behave as partial agonists on the enzymatic activity of the $Na^+,K^+$-ATPase.

To test the affinity for the receptor site of the $Na^+,K^+$-ATPase and the inhibitory activity on the enzyme, the following tests were used: a) displacement of the specific ³H-ouabain binding from the $Na^+,K^+$-ATPase receptor purified according to Jorghensen (Jorghensen P., *BBA*, 1974, 356, 36) and Erdmann (Erdmann E. et al., *Arzneim. Forsh.*, 1984, 34, 1314); b) inhibition of the activity of the purified $Na^+,K^+$-ATPase measured as % of hydrolysis of ³²P-ATP in presence and in absence of the tested compound (Mall F. et al., *Biochem. Pharmacol.*, 1984, 33, 47).

The ability of these compounds to lower blood pressure was tested by using animal models with genetic arterial hypertension, in particular, spontaneous hypertensive rats of the Milan (MHS) (Bianchi G., Ferrari P., Barber B. The Milan Hypertensive strain. In Handbook of hypertension. Vol.4: Experimental and genetic models of hypertension. Ed. W. de jong-Elsevier Science Publishers B.V., 1984: 328–349). The procedure adopted to test the multihypertensive activity of the compounds on the above mentioned model was the following:
systolic blood pressure (SBP) and heart rate (HR) were measured by an indirect tail-cuff method in three-month old hypertensive rats (MHS) before beginning the treatment (basal values). The rats were then subdivided in two groups of at least 7 animals each, one receiving the compound and the other, the control group, receiving only the vehicle. The compound, suspended in Methocel 0.5% (w/v), was administered daily by mouth, for ten days. SBP and HR were measured daily 6 and 24 hours after the treatment. At the end of the ten day treatment period, a washout period of at least two days was carried out, in order to check for how long the SBP was maintained low or the basal values were reestablished.

The affinity and the inhibitory activity of some compounds and of the Ref. compound. in the two tests are shown in the following table:

|  | Binding $^3$H-Ouab. Displacement −log IC50 | Inhibitory Activity −log IC50 |
| --- | --- | --- |
| Comp. I - a | 5.8 | 4.5 |
| Comp. I - b | 5.5 | 4.6 |
| Comp. I - c | 6.3 | 5.1 |
| Comp. I - d | 6.2 | 4.8 |
| Comp. I - f | 5.3 | 4.6 |
| Comp. I - j | 5.4 | 4.1 |
| Comp. I - k | 6.0 | 4.8 |
| Comp. I - n | 5.6 | 4.6 |
| Comp. I - r | 5.4 | 4.5 |
| Comp. I - w | 6.2 | 5.4 |
| Comp. I - x | 6.3 | 5.0 |
| Comp. I - y | 6.3 | 5.2 |
| Comp. I - z | 6.2 | 5.3 |
| Ref. comp. | 5.9 | 5.3 |

The activity of the Ref. compound and some new compound in lowering blood pressure in spontaneous hypertensive MHS rats is shown in the following table:

| SYSTOLIC BLOOD PRESSURE FALL IN SPONTANEOUS HYPERTENSIVE RATS (MHS) | | | | |
| --- | --- | --- | --- | --- |
| COMPOUND | RATS | DOSE* mg/Kg/os | SBP mm Hg | HR beats/min. |
| Controls | 7 | Methocel | 172 +/− 2.0 | 328 +/− 8.6 |
| Comp. I - a | 7 | 10 | 149 +/− 4.3 | 318 +/− 10.2 |
| Comp. I - d | 7 | 10 | 158 +/− 2.5 | 325 +/− 9.3 |
| Comp. I - r | 7 | 10 | 154 +/− 2.4 | 320 +/− 9.6 |
| Ref. comp. | 7 | 10 | 171 +/− 1.9 | 334 +/− 11.7 |

*in Methocel 0.5% w/v

The following examples illustrate the invention without limiting it.

EXAMPLE 1

17β-(3-Furyl)-5β-androstane-3β,14β,17α-triol (I-a)

To a solution of 28 g of 3β,14β,17α-trihydroxy-5β-card-20(22)-enolide (N. Danieli, et al., *Tetrah. Lett.*, 1962, 1281) in 500 ml of anhydrous tetrahydrofuran, 240 ml of 1N cyclohexane solution of diisobutylaluminum hydride, diluted with 300 ml of anhydrous tetrahydrofuran, was added dropwise under stirring, at −20° C. under nitrogen atmosphere. The mixture was stirred for 2 additional hrs when a solution of 3% sulfuric acid was cautiously added and the reaction mixture filtered through celite and the celite washed with methylene chloride. The organic layer was washed in sequence with aqueous sodium hydrogencarbonate solution and water, dried over anhydrous sodium sulfate and evaporated to dryness under reduced pressure. The crude product was purified by flash-chromatography (SiO$_2$) using methylene chloride/ethyl acetate 80/20 as eluant to give 18.0 g of the title compound as a white solid.

$^1$H-NMR (300 MHz, CDCl$_3$, ppm from TMS): 0.85 (3H, s); 0.95 (3H, s); 4.14 (1H, bs); 6.53 (1H, bs); 7.35 (1H, bs); 7.42 (1H, bs).

EXAMPLE 2

3β-(2-Hydroxyethoxy)-17β-(3-furyl)-5β-androstane-14β, 17α-diol (I-b)

To a suspension of 2.20 g of NaH (60% dispersion in mineral oil) in 200 ml of dry, tetrahydrofuran, 6.8 g of 17β-(3-furyl)-5β-androstane-3β,14β,17α-triol (I-a) were added at room temperature, under nitrogen atmosphere and the resulting mixture was refluxed for half an hr; 11.0 ml of bromoacetaldehyde diethylacetal were added and the suspension was kept at reflux temperature for half an hr, then 60 ml of water were added cautiously, and the tetrahydrofuran was distilled under reduced pressure. The residue was extracted with methylene chloride, the organic layer was dried over anhydrous sodium sulfate and evaporated to dryness under reduced pressure. The crude product was purified by flash-chromatography (SiO$_2$)using n-hexane/ ethyl acetate 80/20 as eluant to give 3.0 g of 3β-(2,2-diethoxyethoxy)-17β-(3-furyl)-5β-androstane -14β,17α-diol as a dense oil.

$^1$H-NMR (300 MHz, CDCl$_3$, ppm from TMS): 0.71 (3H, s); 0.95 (3H, s); 2.70 (1H, m); 3.45 (2H, d); 3.53–3.70 (5H, m); 4.60 (1H, m); 6.53 (1H, bs); 7.35 (1H, bs); 7.42 (1H, bs).

A solution of 2.94 g of 3β-(2,2-diethoxyethoxy)-17β-(3-furyl)-5β-androstane-14β,17α-diol in 240 ml of dioxane and 180 ml of a saturated solution of tartaric acid was heated at 60° C. for 2 hrs in a nitrogen atmosphere; 100 ml of water were then added and the residue was extracted with methylene chloride. The organic layer was washed with water, dried over anhydrous sodium sulfate and evaporated to dryness under reduced pressure. The crude product was purified by flash-chromatography (SiO$_2$) using n-hexane/ ethyl acetate 70/30 as eluant to give 1.80 g of 3β-formyl-methoxy-(3-furyl)-5β-androstane-14β, 17α-diol as a white solid.

$^1$H-NMR (300 MHz, CDCl$_3$, ppm from TMS): 0.71 (3H, s); 0.95 (3H, s); 2.71 (1H, m); 3.70 (1H, m); 4.00 (2H, s); 6.53 (1H, bs); 7.35 (1H, bs); 7.42 (1H, bs); 9.75 (1H, s).

To a solution of 1.80 g of 3β-formylmethoxy-(3-furyl)-5β-androstane-14β,17α-diol in 50 ml of methanol, 0.33 g of sodium borohydride were added slowly at 0° C.; after half an hr the temperature of the mixture was left to rise to 25° C. After 2 hrs 20 ml of water were added, the methanol was distilled under reduced pressure, and the mixture was extracted with methylene chloride. The organic layer was washed with water, dried over sodium sulfate and evaporated to dryness under reduced pressure. The crude product was purified by flash-chromatography (SiO$_2$) using n-hexane/ethyl acetate 80/20 as eluant to give 1.56 g of the title compound (I-b) as a white solid.

$^1$H-NMR (300 MHz, CD$_3$OD, ppm from TMS): 0.75 (3H, s); 0.92 (3H, s); 3.42–3.52 (2H, m); 3.61–3.71 (3H, m); 6.58 (1H, bs); 7.31 (1H, bs); 7.34 (1H, bs).

EXAMPLE 3

3β-(3-Aminopropoxy)-17β-(3-furyl)-5β-androstane-14β, 17α-diol (I-c)

To a suspension of 2.5 g of NaH (60% dispersion in mineral oil) in 200 ml of dry tetrahydrofuran 7.8 g of 17β-(3-furyl)-5β-androstane-3β, 14β,17α-triol (I-a) were added at room temperature, under nitrogen atmosphere and the resulting mixture was refluxed for half an hr: 8.0 g of allyl bromide were added and the reflux continued for half an hr. The mixture was quenched with water and the organic solvent was distilled under reduced pressure. The residue was extracted with ethyl acetate, the organic solution was dried over anhydrous sodium sulfate and evaporated to dryness under reduced pressure. The residue was purified by flash-chromatography (SiO$_2$) using n-hexane/ethyl acetate 80/20 as eluant to give 4.0 g of 3β-(prop-2-enoxy)-17β-(3-furyl)-5 β-androstane-14β,17α-diol as a dense oil.

$^1$H-NMR (300 MHz, CDCl$_3$, ppm from TMS): 0.71 (3H, s); 0.95 (3H, s); 2.70 (1H, m); 3.67 (1H, m); 3.90–4.00 (2H, M); 5.13–5.20 (1H, m); 5.23–5.32 (1H, m); 5.86–6.02 (1H, m); 6.53 (1H, bs); 7.35 (1H, bs); 7.42 (1H, bs).

To a solution of 1.4 g of 9-borabicyclo[3.3.1]nonane in 300 ml of dry tetrahydrofuran, 3.9 g of 3β-(prop-2-enoxy)-17β-(3-furyl)-5β-androstane-14β,17α-diol in 50 ml of tetrahydrofuran were added under nitrogen atmosphere, at room temperature. The solution was stirred for 6 hrs, then 6.0 ml of ethanol, 2.0 ml of 6N sodium hydroxide and 4.0 ml of 30% hydrogen peroxide were added. The mixture was stirred at 50° C. for an hr, quenched with a solution of 6.0 g of potassium carbonate in 160 ml of water and the organic solvent distilled under reduced pressure. The residue was extracted with methylene chloride, the organic solution was dried over anhydrous sodium sulfate and evaporated to dryness under reduced pressure. The residue was purified by flash-chromatography (SiO$_2$) using n-hexane/ethyl acetate 70/30 as eluant to give 2.3 g of 3β-(3-hydroxypropoxy)-17β-( 3-furyl)-5β-androstane-14β,17α-diol as a white solid.

$^1$H-NMR (300 MHz, CDCl$_3$, ppm from TMS): 0.71 (3H, s); 0.95 (3H, s); 2.70 (1H, m); 3.57–3.68 (3H, m); 3.91–3.99 (2H, m); 6.53 (1H, bs); 7.35 (1H, bs); 7.42 (1H, bs).

A solution of 0.82 ml of diethyl azodicarboxylate was added dropwise, under nitrogen, to a solution of 2.2 g of 3β(3-hydroxypropoxy)-17β-(3-furyl)-5β-androstane-14β, 17α-diol, 0.75 g of phthalimide and 1.3 g of triphenylphosphine in 10 ml of tetrahydrofuran at room temperature. After 2 hrs the solvent was removed under reduced pressure and the crude product was purified by flash-chromatography (SiO$_2$) using n-hexane/ethyl acetate 80/20 to give 1.9 g of 3β-(3-phthalimidopropoxy)-17β-(3-furyl)-5β-androstane-14β,17α-diol as a white solid.

$^1$H-NMR (300 MHz, CDCl$_3$, ppm from TMS): 0.71 (3H, s); 0.95 (3H, s); 2.70 (1H, m); 3.38–3.50 (2H, m); 3.55 (1H, m); 3.83 (2H, t); 6.53 (1H, bs); 7.35 (1H, bs); 7.42 (1H, bs); 7.71-7.77 (2H, m); 7.83–7.94 (2H, m).

To a solution of 1.9 g of 3β-(3-phthalimidopropoxy)-17β-(3-furyl)-5β-androstane-14β, 17α-diol in 50 ml of ethanol, 0.83 g of hydrazine hydrate were added at room temperature. The mixture was kept at reflux temperature for 4 hrs, then 50 ml of water were added and the ethanol distilled under reduced pressure. The residue was extracted with methylene chloride, the organic solution was washed with water, dried over anhydrous sodium sulfate and evaporated to dryness under reduced pressure. The crude residue was purified by flash-chromatography (SiO$_2$) using methylene chloride/methanol 90/10 as eluant to give 1.0 g of the title compound (I-c) as a white solid.

$^1$H-NMR (300 MHz, CDCl$_3$, ppm from TMS): 0.85 (3H, s); 0.95 (3H, s); 2.82 (2H, t); 3.42–3.51 (2H, t); 3.62 (1H, bs); 6.53 (1H, bs); 7.35 (1H, bs); 7.42 (1H, bs).

EXAMPLE 4

3β-(2-(1-Pyrrolidinyl)ethoxy)-17β-(3-furyl)-5β-androstane-14β,17α-diol (I-d)

To a suspension of 1.60 g of NaH (60% dispersion in mineral oil) in 140 ml of dry tetrahydrofuran, 5.40 g of 17β-(3-furyl)-5β-androstane-3β,14β,17α-triol (I-a) were added at room temperature, under nitrogen atmosphere. The mixture was refluxed for 3 hrs, then 13.4 g of 1-(2-chloroethyl)pyrrolidine were added; the suspension was kept at reflux temperature for 2 hrs; 100 ml of water were added cautiously and the tetrahydrofuran was distilled at reduced pressure. The residue was extracted with methylene chloride, the organic layer was dried over anhydrous sodium sulfate and evaporated to dryness, under reduced pressure. The crude product was purified by flash-chromatography (SiO$_2$) using methylene chloride/methanol 90/10 as eluant to give 0.96 g of the title compound (I-d) as a white solid.

$^1$H-NMR (300 MHz, CDCl$_3$, ppm from TMS): 0.85 (3H, s); 0.95 (3H, s); 2.52–2.70 (6H, m); 3.48–3.59 (2H, m); 3.62 (1H, bs): 6.55 (1H, bs); 7.35(1H, bs); 7.42 (1H, bs).

EXAMPLE 5

17β-(3-Furyl)-17α-methoxy-5β-androstane-3β,14β-diol (I-e)

To a solution of 1.0 g of dimethyl-tert-butylsilylchloride and 0.91 g of imidazole in 3 ml of dry dimethylformamide, 0.50 g of 17β-(3-furyl)-5β-androstane-3β,14β, 17α-triol (I-a) were added under nitrogen atmosphere, at room temperature. The resulting mixture was stirred for 6 hrs, then it was diluted with water and extracted with ethyl acetate; the combined extracts were dried over anhydrous sodium sulfate and evaporated to dryness under reduced pressure. The crude product was purified by flash-chromatography (SiO$_2$) using cyclohexene/ethyl acetate 95/5 as eluant to give 0.43 g of 3β-(dimethyl-tert-butylsilyloxy)-17β-(3-furyl)-5 β-androstane-14β,17α-diol as a white solid.

$^1$H-NMR (300 MHz, CDCl$_3$, ppm from TMS): 0.03 (6H, s); 0.71 (3H, s); 0.91 (9H, s); 0.95 (3H, s); 2.68 (1H, s); 4.04 (1H, m); 6.55 (1H, bs); 7.38 (1H, bs); 7.43 (1H, bs).

To a suspension of 0.17 g of KH (20% dispersion in mineral oil) in 5 ml of dry tetrahydrofuran, 0.35 g of 3β-(dimethyl-tert-butylsilyloxy)-17β-(3-furyl)-5β-androstane-14β,17α-diol were added at room temperature, under nitrogen atmosphere. The mixture was kept at room temperature for half an hr, then 0.053 ml of methyl iodide were added: after 2 hrs 5 ml of water were added cautiously and the tetrahydrofuran was distilled at reduced pressure. The residue was extracted with methylene chloride, the organic layer was dried over anhydrous sodium sulfate and evaporated to dryness, under reduced pressure. The crude product was purified by flash-chromatography (SiO$_2$) using cyclohexene/ethyl acetate 95/5 as eluant to give 0.32 g of 3β-(dimethyl-tert-butylsilyloxy)-17β-(3-furyl)-17α-methoxy-5β-androstan-14β-ol as a white solid.

$^1$H-NMR (300 MHz, CDCl$_3$, ppm from TMS): 0.03 (6H, s); 0.95–1.01 (15H, m); 3.0 (3H, s); 4.05 (1H, bs); 6.41 (1H, bs); 7.38 (1H, bs); 7.41 (1H, bs).

To a solution of 0.32 g of 3β-(dimethyl-tert-butylsilyloxy)-17β-(3-furyl)-17α-methoxy-5β-androstan-14β-ol in 5 ml of tetrahydrofuran, 0.85 g of tetrabutylammonium fluoride trihydrate were added. The resulting mixture was kept at reflux temperature for 20 hrs, then 30 ml of water were added and the tetrahydrofuran was distilled under reduced pressure. The residue was extracted with methylene chloride, the organic layer was dried over anhydrous sodium sulfate and evaporated to dryness. The crude product was purified by flash-chromatography (SiO$_2$) using methylene chloride/methanol 85/15 as eluant to give 0.20 g of the title compound (I-e) as a white solid.

$^1$H-NMR (300 MHz, CDCl$_3$, ppm from TMS): 0.93 (3H, s); 0.95 (3H, s); 3.10 (3H, s); 4.14 (1H, bs); 6.42 (1H, bs); 7.39 (1H, bs); 7.41 (1H, bs).

EXAMPLE 3

3β-(2-(1-Pyrrolidinyl)ethoxy)-17β-(3-furyl)-17α-methoxy-5β-androstan-14β-ol (I-f)

The title compound (I-f) (0.62 g) was obtained as a white solid from 17β-(3-furyl)-17α-methoxy-5β-androstane-3β,14β-diol (I-e) (0.60 g) using the same procedure described in Ex. 4.

$^1$H-NMR (300 MHz, CDCl$_3$, ppm from TMS): 0.93 (3H, s); 0.95 (3H, s); 2.52–2.70 (6H, m); 3.0 (3H, s); 3.48–3.59 (2H, m); 3.62 (1H, bs); 6.42 (1H, bs); 7.39 (1H, bs); 7.41 (1H, bs).

EXAMPLE 7

17β-(3-furyl)-17α-(2-(1-pyrrolidinyl)ethoxy)-5β-androstane-3β,14β-diol (I-g)

To a suspension of 0.35 g of NaH (60% dispersion in mineral oil) in 30 ml of dry tetrahydrofuran 0.42 g of 3β-(dimethyl-tert-butylsilyloxy)-17β-(3-furyl)-5β-androstane-14β,17α-diol were added at room temperature, under nitrogen atmosphere. The mixture was refluxed for 6 hrs, then 1.35 g of 1-(2-chloroethyl)pyrrolidine were added; the suspension was refluxed for 4 hrs, then 25 ml of water were added cautiously and the tetrahydrofuran was distilled at reduced pressure. The residue was extracted with methylene chloride, the organic layer was dried over anhydrous sodium sulfate and evaporated to dryness under reduced pressure. The crude product was purified by flash-chromatography (SiO$_2$) using methylene chloride/methanol 90/10 as eluant to give 0.32 g of 3β-(dimethyl-tert-butylsilyloxy)-17β-(3-furyl)-17 α-(2-(1-pyrrolidinyl)ethoxy)-5β-androstan-14β-ol as a white solid.

$^1$H-NMR (300 MHz, CDCl$_3$, ppm from TMS): 0.03 (6H, s); 0.92 (3H, s); 0.91 (9H, s); 0.99 (3H, s); 2.48–2.52 (6H, m); 3.19–3.31 (2H, m); 4.04 (1H, m); 6.40 (1H, bs); 7.38 (2H, bs).

The title compound (I-g) (0.18 g) was obtained as a white solid from 3β-(dimethyl-tert-butylsilyloxy)-17β-(3-furyl)-17α-(2-(1-pyrrolidinyl)ethoxy)-5β-androstan-14β-ol (0.31 g) deprotecting the dimethyl-tert-butylsilyloxy group with tetrabutylammonium fluoride trihydrate as described in Ex. 5.

$^1$H-NMR (300 MHz, CDCl$_3$, ppm from TMS): 0.92 (3H, s); 0.93 (3H, s); 2.48–2.52 (6H, m); 3.19–3.31 (2H, m); 4.14 (1H, bs); 6.40 (1H, bs); 7.38 (2H, bs).

EXAMPLE 8

3β,17α-Bis(2-(1-pyrrolidinyl)ethoxy)-17β-(3-furyl)-5β-androstan-14β-ol (I-h)

The title compound (I-h) (0.25 g) was obtained as a white solid from 17β-(3-furyl)-5β-androstane-3β,14β,17α-triol (I-a) (0.22 g) using the same procedure described in Ex. 4, but the reaction was kept at reflux temperature for 24 hrs, instead of 2 hrs.

$^1$H-NMR (300 MHz, CDCl$_3$, ppm from TMS): 0.92 (3H, s); 0.93 (3H, s); 2.48–2.70 (12H, m); 3.19–3.31 (2H, m); 3.48–3.59 (2H, m); 3.62 (1H, bs); 6.40 (1H, bs); 7.38 (2H, bs).

EXAMPLE 9

3β,17α-Bis(3-aminopropoxy)-17β-(3-furyl-5β-androstan-14β-ol (I-i)

To a solution of 0.58 g of 17β-(3-furyl)-5β-androstane-3β,14β,17α-triol (I-a) in 50 ml of dry tetrahydrofuran, 1.26 g of sodium hydride (60% dispersion in mineral oil) were added under nitrogen atmosphere, at room temperature and the resulting mixture was stirred at reflux temperature for 6 hrs; 4.0 g of allyl bromide were added and the reflux continued for further 4 hrs. The mixture was quenched with water and the organic solvent was distilled under reduced pressure. The residue was extracted with ethyl acetate, the organic solution was dried over anhydrous sodium sulfate and evaporated to dryness under reduced pressure. The residue was purified by flash-chromatography (SiO$_2$) using n-hexane/ethyl acetate 80/20 as eluant to give 0.53 g of 3β,17α-bis(prop-2-enoxy)-17β-(3-furyl)- 5β-androstan-14β-ol as a dense oil.

$^1$H-NMR (300 MHz, CDCl$_3$, ppm from TMS):0.87 (3H, s); 0.95 (3H, s); 3.67 (1H, m); 3.89–4.02 (4H, m); 5.08–5.25 (2H, m); 5.27–5.36 (2H, m); 5.86–6.04 (2H, m); 6.40 (1H, bs); 7.38 (2H, bs).

To a solution of 0.38 g of 9-borabicyclo[3.3.1 ]nonane in 70 ml of dry tetrahydrofuran, 0.49 g of 3β,17α-bis(prop-2-enoxy)-17β-(3-furyl)-5β-androstan-14β-ol in 20 ml of tetrahydrofuran were added under nitrogen atmosphere, at room temperature. The solution was stirred for 6 hrs, then 1.5 ml of ethanol, 0.5 ml of 6N sodium hydroxide and 1 ml of 30% hydrogen peroxide were added. The mixture was stirred at 50° C. for one hr, a solution of 1.5 g of potassium carbonate in 40 ml of water were added and the organic solvent distilled under reduced pressure. The residue was extracted with methylene chloride, the organic solution was dried over anhydrous sodium sulfate and evaporated to dryness under reduced pressure. The residue was purified by flash-chromatography (SiO$_2$) using n-hexane/ethyl acetate 70/30 as eluant to give 0.25 g of 3β,17α-bis(3-hydroxypropoxy)-17β-(3-furyl)-5β-androstan -14β-ol as a white amorphous solid.

$^1$H-NMR (300 MHz, CDCl$_3$, ppm from TMS):0.88 (3H, s); 0.95 (3H, s); 3.57–3.68 (5H, m); 3.93–3.99 (4H, m); 6.40 (1H, bs); 7.38 (2H, bs).

A solution of 0.16 ml of diethyl azodicarboxylate was added dropwise, under nitrogen, to a solution of 0.24 g of 31β,17α-bis(3-hydroxypropoxy)-17β-(3-furyl)-5β-androstan-14β-ol, 0.44 g of phthalimide and 0.15 g of triphenylphosphine in 2 ml of tetrahydrofuran at room temperature. After 2 hrs the solvent was removed under reduced pressure and the crude product was purified by flash-chromatography (SiO$_2$) using the n-hexane/ethyl acetate 80/20 to give 0.15 g of 3β,17α-bis(3-phthalimidopropoxy)-17β-(3-furyl)-5β-androstan-14β-ol as a white solid.

$^1$H NMR (300 MHz, CDCl$_3$, ppm from TMS):0.88 (3H, s); 0.95 (3H, s); 3.38–3.50 (4H, m); 3.55 (1H, m); 3.83 (4H, m); 6.40 (1H, bs); 7.38 (2H, bs); 7.71–7.77 (4H, m); 7.83–7.94 (4H, m).

To a solution of 0.15 g of 3β,17α-bis(3-phthalimidopropoxy)-17β-(3-furyl)- 5β-androstan-14β-ol in 18 ml of ethanol, 0.65 g of hydrazine hydrate were added at room temperature. The mixture was kept at reflux temperature for 4 hrs, then 10 ml of water were added and the ethanol distilled under reduced pressure. The residue was extracted with methylene chloride, the organic solution was washed with water, dried over anhydrous sodium sulfate and evaporated to dryness under reduced pressure. The crude residue was purified by flash-chromatography (SiO$_2$) using methylene chloride/methanol 90/10 as eluant to give 0.071 g of the title compound (I-i) as a white solid.

$^1$H-NMR (300 MHz, CDCl$_3$, ppm from TMS): 0.92 (3H, s); 0.93 (3H, s); 2.80–2.95 (4H, m); 3.17–3.30 (2H, m); 3.42–3.55 (2H, m); 3.62 (1H, bs); 6.40 (1H, bs); 7.38 (2H, bs).

EXAMPLE 10

14β,17α-Dihydroxy-17β-(3-furyl)-5β-androstan-3-one (I-j)

To a solution of 8.76 g of 17β-(3-furyl)-5β-androstane-3β,14β,17α-triol (I-a) in 150 ml of methylene chloride, 4.20 g of 4-methylmorpholine N-oxide, 0.45 g of tetrapropylammonium perruthenate and 9.0 g of powdered 4Å molecular sieves were added at room temperature. After 4 hrs the solvent was evaporated to dryness under reduced pressure and the crude product purified by flash-chromatography (SiO$_2$) using n-hexane/ethyl acetate 70/30 as eluant to give 8.37 g of the title compound (I-j) as a white solid.

$^1$H-NMR (300 MHz, CDCl$_3$, ppm from TMS): 0.89 (3H, s); 1.03 (3H, s); 2.69 (1H, t); 6.55 (1H, bs); 7.37 (1H, bs); 7.43 (1H, bs).

EXAMPLE 11

3-Guanidinoimino-17β-(3-furyl)-5β-androstane-14β,17α-diol (I-k)

A solution of 0.34 g of 14β,17α-dihydroxy-17β-(3-furyl)-5β-androstan-3-one (I-j) in 5 ml of ethanol was added to a solution of 0.26 g of aminoguanidine hydrogencarbonate and 19 ml of 0.1N NaOH. The resulting mixture was kept at reflux temperature for half an hr and the ethanol evaporated to dryness under reduced pressure. The precipitate was filtered, washed in sequence with water and diethyl ether and dried in oven at 60° C. under reduced pressure: 0.33 g of the title compound (I-k) were obtained as a white solid.

$^1$H-NMR (300 MHz, DMSO-d6, ppm from TMS): 0.61 (3H, s); 0.87 (3H, s); 3.57 (1H, s); 4.55 (1H, s); 5.03 (2H, bb); 5.45 (2H, bb); 6.55 (1H, bs); 7.32 (1H, bs); 7.37 (2H, bs).

EXAMPLE 12

17β-(3-Furyl)-5β-androstane-3α,14β,17α-triol (I-l)

To a solution of 6.0 g of 14β,17α-dihydroxy-17β-(3-furyl)-5β-androstan-3-one (I-j) in 40 ml of dry tetrahydrofuran at –78° C., a solution of 13.10 g of tri-tert-butoxyaluminum hydride in dry tetrahydrofuran was added dropwise. The mixture was stirred for 20 hrs, the temperature raised to 25° C., then 80 ml of water were added. The aluminum salts were filtered on a celite cake and washed with methanol. The solution was filtered, concentrated under reduced pressure and extracted with methylene chloride. The organic layer was dried over sodium sulfate and evaporated to dryness under reduced pressure to give 5.80 g of the title compound (I-l) as a white solid.

$^1$H-NMR (300 MHz, CDCl$_3$, ppm from TMS): 0.87 (3H, s); 0.92 (3H, s); 3.61–3.75 (1H, m); 6.52 (1H, bs); 7.35 (1H, bs); 7.42 (2H, bs).

EXAMPLE 13

3α-(2-(1-Pyrrolidinyl)ethoxy)-17β-(3-furyl)-5β-androstane-14β,17α-diol (I-m)

The title compound (I-m) (0.22 g) was obtained as a white solid from 17β-(3-furyl)-5β-androstane-3α,14β,17α-triol (I-l) (0.60 g) using the same procedure described in Ex. 4.

$^1$H-NMR (300 MHz, CDCl$_3$, ppm from TMS): 0.87 (3H, s); 0.92 (3H, s); 2.52–2.70 (6H, m); 3.22–3.37 (1H, m); 3.48–3.59 (2H, m); 6.53 (1H, bs); 7.35 (1H, bs); 7.42 (2H, bs).

EXAMPLE 14

17β-(4-Pyridazinyl)-5β-androstane-3β,14β,17α-triol (I-n)

A solution of 5.2 g of sodium acetate and 10.0 g of 17β-(3-furyl)-5β-androstane-3β,14β,17α-triol (I-a) in 100 ml of 1,4-dioxane/water (13/1) was cooled and kept at 0° C., while a solution of 5.7 g of N-bromosuccinimide in 50 ml of 1,4-dioxane/water (13:1) was added. After 0.5 hr a solution of hydrazine (20 ml) in 1,4-dioxane/water (40 ml) was slowly added. After 1 hr the mixture was diluted with 200 ml of water and extracted with chloroform/methanol 80/20; the combined extracts were dried over anhydrous sodium sulfate and evaporated to dryness under reduced pressure. The crude product was purified by flash-chromatography (SiO$_2$) using chloroform/methanol 90/10 as eluant to give 3.5 g of the title compound (I-n) as a white solid.

$^1$H-NMR (300 MHz, CD$_3$OD, ppm from TMS): 0.61 (3H, s); 0.98 (3H, s); 2.21 (1H, m); 4.09 (1H, m); 7.88 (1H, m); 9.00 (1H, d); 9.35 (1H, m).

EXAMPLE 15

14β,15β-Epoxy-17β-(3-furyl)-5β-androstane-3β,17α-diol (I-o)

A mixture of 10.0 g of 3β-hydroxy-14β,15β-epoxy-5β-card-20(22)-enolide (H. Ishii, et al., *Chem. Pharm. Bull*, 1963, 11,576) and 10.0 g of selenium dioxide in 300 ml of dioxane was heated at reflux temperature for 24 hrs. The mixture was filtered on a celite pad, the solvent evaporated under reduced pressure and the residue partitioned between chloroform and water. The organic phase was dried on sodium sulfate, evaporated to dryness and the residue purified by flash-chromatography (SiO$_2$) using methylene chloride/ethyl acetate 70/30 as eluant to give 6.0 g of 3β,17α-dihydroxy-14β,15β-epoxy-5 β-card-20(22)-enolide as a white solid.

$^1$H-NMR (300 MHz, CDCl$_3$, ppm from TMS): 0.81 (3H, s); 1.00 (3H, s); 2.22 (1H, d); 2.60 (1H, d); 3.47 (1H, bs); 4.16 (1H, bs); 4.30–4.50 (2H, m); 5.15 (1H, bs).

3β,17α-dihydroxy-14β,15β-epoxy-5β-card-20(22)-enolide (5.0 g) was reduced with diisobutylalluminum hydride as described in Ex. 1 to give 3.0 g of the title compound (I-o) as a white solid.

$^1$H-NMR (300 MHz, CDCl$_3$, ppm from TMS): 0.81 (3H, s); 1.00 (3H, s); 2.22 (1H, d); 2.60 (1H, d); 3.47 (1H, bs); 4.16 (1H, bs); 6.54 (1H, bs); 7.29 (1H, bs); 7.37 (1H, bs).

EXAMPLE 16

3β-(2-(1-Pyrrolidinyl)ethoxy)-14β,15β-epoxy-17β-(3-furyl)-5β-androstan-17α-ol (I-p)

The title compound (I-p) (0.080 g) was obtained as a white solid from 14β,15β-epoxy-17β-(3-furyl)-5β-androstane-3β,17α-diol (I-o) (0.28 g) using the same procedure described in Ex. 4.

¹H-NMR (300 MHz, CDCl₃, ppm from TMS): 0.79 (3H, s); 1.01 (3H, s); 2.32 (1H, d); 2.45–2.86 (7H, m); 3.48 (1H, bs); 3.53 (1H, bs); 3.75 (2H, t); 6.54 (1H, bs); 7.29 (1H, bs); 7.37 (1H, bs).

EXAMPLE 17

3β-Mercapto-14β,15β-epoxy-17β-(3-furyl)-5β-androstan-17α-ol (I-q)

Disopropyl azodicarboxylate (8.9 ml) was added to a solution of 11.2 g of triphenylphosphine in 200 ml of tetrahydrofuran at 0° C. and the mixture was stirred for 30'. To this mixture a solution of 5.0 g of 14β,15β-epoxy-17β-(3-furyl)-5β-androstane-3α,17α-diol (prepared from 14β,15β-epoxy-17β-(3-furyl)-17α-hydroxy-5β-androstan-3-one, as described in Ex. 12, that had been prepared from 14β,15β-epoxy-17β-(3-furyl)-5β-androstane-3β,17α-diol (I-o) as described in Ex. 10) and 5.20 ml of thiolacetic acid in 250 ml of tetrahydrofuran was added dropwise and the resulting mixture was stirred for one hr at room temperature. The solvent was evaporated to dryness under reduced pressure and the crude product was purified by flash-chromatography (SiO₂) using n-hexane/ethyl acetate 95/5 as eluant to give 4.2 g of 3β-acetylthio-14β,15β-epoxy-17β-(3-furyl)-5β-androstan-17α-ol as a white solid.

¹H-NMR (300 MHz, CDCl3, ppm from TMS): 0.89 (3H, s): 1.06 (3H, s); 2.25–2.35 (4H, m); 2.60 (1H, d); 3.47 (1H, bs); 4.08 (1H, bs); 6.60 (1H, bs); 7.29 (1H, bs); 7.37 (1H, bs).

A solution of 4.0 g of 3β-acetylthio-14β,15β-epoxy-17β-(3-furyl)-5β-androstan-17 α-ol in 50 ml of methanol, was saturated with gaseous ammonia and kept for 3 hrs at room temperature. The mixture was evaporated to dryness under reduced pressure and purified by flash-chromatography (SiO₂) using n-hexane/ethyl acetate 95/5 as eluant to give 3.5 g of the title compound as a white solid.

¹H-NMR (300 MHz, CDCl₃, ppm from TMS): 0.89 (3H, s); 1.06 (3H, s); 2.22 (1H, d); 2.60 (1H, d); 3.47 (1H, bs); 3.62 (1H, bs); 6.60 (1H, bs); 7.29 (1H, bs); 7.37 (1H, bs).

EXAMPLE 18

3β-(3-Aminopropylthio)-14β,15β-epoxy-17β-(3-furyl)-5β-androstan-17α-ol oxalate (I-r)

To a solution of 1.14 g of 3β-mercapto-14β,15β-epoxy-17β-(3-furyl)-5β-androstan-17 α-ol (Ex. 17) and 0.67 ml of 3-chloropropylamine in 10 ml of tetrahydrofuran under nitrogen atmosphere, at room temperature, 0.063 g of sodium hydride (60% dispersion in mineral oil) were added. The reaction mixture was stirred for 40 hrs at room temperature then diluted with water and extracted with ethyl acetate. The organic layer was dried over sodium sulfate and evaporated to dryness under reduced pressure. The crude product was purified by flash-chromatography (SiO₂) using methylene chloride/methanol/30% ammonia solution 95/5/1 as eluant and successively treated with oxalic acid to give 0.40 g of the title compound (I-r) as a white solid.

¹H-NMR (300 MHz, CDCl₃, ppm from TMS): 0.79 (3H, s); 1.01 (3H, s); 2.33 (1H, d); 2.51–2.64 (3H, m); 2.83 (2H, bt); 3.22 (1H, bs); 3.49 (1H, bs); 6.52 (1H, bs); 7.29 (1H, bs); 7.37 (1H, bs).

EXAMPLE 29

3β-(2-(1-Pyrrolidinyl)ethylthio)-14β,15β-epoxy-17β-(3-furyl)-5β-androstan-17α-ol (I-s)

The title compound (I-s) (0.19 g) was obtained as a pale yellow solid from 0.25 g of 3β-mercapto-14β,15β-epoxy-17β-(3-furyl)-5β-androstan-17α-ol (Ex. 17) and 1-(2-chloroethyl)pyrrolidine (0.63 g) using the same procedure described in Ex. 18.

¹H-NMR (300 MHz, CDCl₃, ppm from TMS): 0.81 (3H, s); 1.0 (3H, s); 2.22 (1H, d); 2.51–2.61 (5H, m); 2.65–2.69 (4H, bt); 3.49 (1H, bs); 3.76 (1H, bs); 6.52 (1H, bs); 7.31 (1H, bs); 7.37 (1H, bs).

EXAMPLE 20

17α-(3-Furyl)-5β-androstane-3β,14β,17β-triol (I-t)

The title compound (I-t) (0.70 g) was obtained as white solid from 1.1 g of 3β,14β,17β-trihydroxy-5β,17α-card-20(22)-enolide (Saito, et al., Chem. *Pharm. Bull.* 1970, 18, 629) following the same procedure as described in Ex. 1.

¹H-NMR (300 MHz, CDCl₃, ppm from TMS): 0.98 (3H, s); 1.05 (3H, s); 2.97 (1H, bs); 3.68 (1H, bs); 4.14 (1H, m); 6.39 (1H, m); 7.39 (2H, m).

EXAMPLE 21

3β-(2-(1-Pyrrolidinyl)ethoxy)-17α-(3-furyl)-5β-androstane-14β,17β-diol (I-u)

The title compound (I-u) (0.32 g) was obtained as a white solid from 17α-(3-furyl)-5β-androstane-3β,14β,17β-triol (I-t) (1.0 g) using the same procedure described in Ex. 4.

¹H-NMR (300 MHz, CDCl₃, ppm from TMS): 0.96 (3H, s); 1.03 (3H, s); 2.52–2.70 (6H, m); 3.48–3.59 (2H, m); 3.62 (1H, bs); 6.38 (1H, bs); 7.39 (2H, bs).

EXAMPLE 22

3β,17β-Bis(2-(1-pyrrolidinyl)ethoxy)-17α-(3-furyl)-5β-androstan-14β-ol (I-v)

The title compound (I-v) (0.31 g) was obtained as white solid from 17α-(3-furyl)-5β-androstane-3β,14β,17β-triol (I-t) (0.30 g) using the same procedure described in Ex. 8.

¹H-NMR (300 MHz, CDCl₃, ppm from TMS): 1.01 (3H, s); 1.03 (3H, s); 2.48–2.70 (12H, m); 3.19–3.31 (2H, m); 3.48–3.59 (2H, m); 3.62 (1H, bs); 6.23 (1H, bs); 7.39 (2H, bs).

EXAMPLE 23

3β-(2-(2-(1-Pyrrolidinyl)ethoxy)ethoxy)-17β-(3-furyl)-5β-androstane-14β,17α-diol (I-w)

To a solution of 0.85 g of 3β-(2-hydroxyethoxy)-17β-(3-furyl)-5β-androstane-14β,17α-diol (I-b), in 9 ml of dry pyridine, 0.76 g of tosyl chloride were slowly added at room temperature. After 5 hrs stirring, 15 ml of water and 60 ml of ethyl acetate were added, the organic layer was washed with water and dried over anhydrous sodium sulfate to give 1.1 g of 3β-(2-tosyloxyethoxy)-17β-(3-furyl)-5β-androstane-14β,17α-diol as a white solid.

¹H-NMR (300 MHz, CDCl₃, ppm from TMS): 0.85 (3H, s); 0.90 (3H, s); 2.48 (3H, s); 3.52–3.62 (3H, m); 4.15–4.20 (2H, m); 6.53 (1H, bs); 7.30–7.38 (3H, m); 7.42 (1H, bs);7.78–7.83 (2H, d).

To a suspension of 0.1 g of NaH (60% dispersion in mineral oil) in 10 ml of anhydrous dimethylformamide, 0.2 g of 1-(2-hydroxyethyl)pyrrolidine were added at room temperature in a nitrogen atmosphere. The mixture was kept at reflux temperature for 2 hrs, then 0.55 g of 3β-(2-tosyloxyethoxy)-17β-(3-furyl)-5β-androstane-14β,17α-diol were added. The mixture was kept at reflux temperature for 4 hrs; then 30 ml of water were added cautiously. The residue was extracted with methylene chloride, the organic layer was washed with water, dried over anhydrous sodium sulfate and evaporated to dryness under reduced pressure. The crude product was purified by flash-chromatography (SiO$_2$) using methylene chloride/methanol 95/5 as eluant to give 0.36 g of the title compound (I-w) as a light yellow solid.

$^1$H-NMR (300 MHz, CDCl$_3$, ppm from TMS): 0.85 (3H, s); 0.90 (3H, s); 2.52–2.67 (4H, m); 2.67–2.78 (2H, m); 3.51–3.58 (2H, m); 3.58–3.68 (5H, m); 6.53 (1H, bs); 7.37 (1H, bs); 7.42 (1H, bs).

EXAMPLE 24

3β-(2-Methylaminoethoxy)-17β-(3-furyl)-5β-androstane-14β,17α-diol (I-x)

To 18 ml of a solution of methylamine 3.2M in methanol, 0.30 g of 3β-(2-tosyloxyethoxy)-17β-(3-furyl)-5β-androstane-14β,17α-diol, prepared as an intermediate in Ex. 23, were added. The solution was kept at reflux temperature under nitrogen for 11 hrs and then evaporated to dryness under reduced pressure. The resulting solid was washed with n-hexane to give 0.16 g of the title compound (I-x) as a light yellow pasty solid.

$^1$H-NMR (300 MHz, CDCl$_3$, ppm from TMS): 0.85 (3H, s); 0.92 (3H, s); 2.54 (3H, s); 2.82 (2H, t); 3.00–3.08 (2H, m); 3.68 (1H, bs); 6.53 (1H, s); 7.37 (1H, s); 7.42 (1H, s).

EXAMPLE 25

3β-(3-Guanidinopropoxy)-17β-(3-furyl)-5β-androstane-14β,17α-diol (I-y)

To a solution of 0.43 g of 3β-(3-aminopropoxy)-17β-(3-furyl)-5β-androstane-14β,17α-diol (I-c) in 20 ml of absolute ethanol 0.35 g of 3,5-dimethyl-1-pyrazolylformamidinium nitrate were added and the mixture was kept at reflux temperature for 24 hrs; the ethanol was concentrated under reduced pressure and 0.39 g of the title compound (I-y) crystallized as a white solid.

$^1$H NMR: (300 MHz, DMSO-d6, ppm from TMS): 0.70 (3H, s); 0.85 (3H, s); 3.14 (2H, m); 3.35 (2H, m); 3.54 (1H, bs); 3.82 (1H, bs); 6.56 (1H, bs); 7.42 (1H, bs); 7.55 (1H, bs).

EXAMPLE 26

3β-(2,3-Diaminopropoxy)-17β-(3-furyl)-5β-androstane-14β,17α-diol (I-z)

To a mixture of 0.84 g of N-Methylmorpholine-N-oxide, 7 ml of water, 15 ml of acetone and 2 ml of a 0.06M ethereal osmium tetroxide solution, 2.5 g of 3β-(prop-2-enoxy)-17β-(3-furyl)-5β-androstane-14β,17α-diol, prepared as an intermediate in Ex. 3, dissolved in 33 ml of tert-butanol were added at room temperature. The mixture was left on standing for 20 hrs, 50 ml of a saturated sodium hydrosulfite solution and 3 g of celite were added, the mixture was stirred for 2 hrs and then filtered. The organic solvent was distilled under reduced pressure, the aqueous phase was extracted with methylene chloride, the organic layer was dried over anhydrous sodium sulfate and evaporated to dryness under reduced pressure. The crude product was purified by flash-chromatography (SiO$_2$) using n-hexane/ethyl acetate 20/80 as eluant to give 2.2 g of 3β-(2,3-dihydroxypropoxy)-17β-(3-furyl)-5β-androstane-14β,17α-diol as a white solid.

$^1$H NMR (300 MHz, CDCl$_3$, ppm from TMS): 0.85 (3H, s); 0.95 (3H, s); 3.46–3.60 (2H, m); 3.68 (1H, bs); 3.70–3.79 (2H, m); 3.82–3.92 (1H, m); 6.53 (1H, bs); 7.37 (1H, bs); 7.42 (1H, bs).

To a solution of 0.82 g of 3β-(2,3-dihydroxypropoxy)-17β-(3-furyl)-5β-androstane-14β, 17α-diol, in 6.4 ml of dry pyridine, 0.8 g of tosyl chloride were added at a temperature of 0° C. After 5 hrs 15 ml of water and 60 ml of ethyl acetate were added, the organic layer was washed with water, dried over anhydrous sodium sulfate and evaporated to dryness under reduced pressure. The crude product was purified by flash-chromatography (SiO$_2$) using n-hexane/ethyl acetate 80/20 as eluant to give 1.2 g of 3β-(2,3-ditosyloxypropoxy)-17β-(3-furyl)-5β-androstane-14β,17α-diol as a white solid.

$^1$H NMR (300 MHz, CDCl$_3$, ppm from TMS): 0.85 (3H, s); 0.88 (3H, s); 2.45 (6H, bs); 3.45–3.55 (3H, m); 4.05–4.18 (2H, m); 4.62 (1H, bs); 6.58 (1H, bs); 7.30–7.43 (6H, m); 7.70–7.82 (4H, m).

To a solution of 1.2 g of 3β-(2,3-ditosyloxypropoxy)-17β-(3-furyl)-5β-androstane- 14β,17α-diol in 9 ml of dimethylsulfoxide 1 g of sodium azide were added at room temperature. The solution was kept at reflux temperature for 3 hrs, then 5 ml of water were added and the residue was extracted with methylene chloride. The organic layer was washed with water, dried over anhydrous sodium sulfate and evaporated to dryness under reduced pressure. The crude product was purified by flash-chromatography (SiO$_2$) using n-hexane/ethyl acetate 80/20 as eluant to give 0.7 g 3β-(2,3-diazidopropoxy)-17β-(3-furyl)-5β-androstane -14β,17α-diol.

$^1$H NMR: (300 MHz, CDCl$_3$, ppm from TMS): 0.86 (3H, s); 0.94 (3H, s); 3.4–3.7 (6H, m); 6.53 (1H, bs); 7.37 (1H, bs); 7.42 (1H, bs).

A solution of 0.42 g of 3β-(2,3-diazidopropoxy)-17β-(3-furyl)-5β-androstane-14β,17α-diol in 10 ml of diethyl ether is added to a suspension of 0.15 g of lithium aluminum hydride in 6 ml of diethyl ether.

The mixture was kept at reflux temperature for 12 hrs then in succession were added 0.32 ml of water, 0.32 ml of sodium hydroxide (water solution 10%) and 1.5 ml of water. The mixture was filtered over a celite cake, the organic solution was washed with water, dried over sodium sulfate and evaporated to dryness under reduced pressure. The crude residue was purified by flash-chromatography (SiO$_2$) using methylene chloride/methanol/30% ammonia solution 90/10/1 as eluant to give 0.34 g of the title compound (I-z) a white solid.

$^1$H NMR (300 MH$_z$, CDCl$_3$, ppm from TMS): 0.84 (3H, s); 0.90 (3H, s); 2.70–3.50 (5H, m); 3.68 (1H, bs); 6.53 (1H, bs); 7.37 (1H, bs); 7.42 (1H, bs).

We claim:

1. A 17-(4-pyridazinyl)-5β,14β-androstane derivative of formula (I):

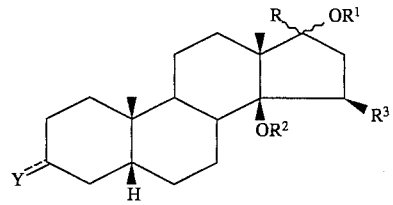

wherein:

the symbol ⁓ means that the substituents in position 17 can have an α or β configuration;

the symbol --- represents a single or double bond;

Y is oxygen or guanidinoimino, when --- in position 3 is a double bond;

Y is hydroxyl, $OR^4$ or $SR^4$, when --- in position 3 is a single bond and can have an α or β configuration;

R is an unsubstituted or substituted 4-pyridazinyl group;

$R^1$ is hydrogen; methyl; ethyl or n-propyl substituted by OH or $NR^5R^6$;

$R^2$ is hydrogen or together to $R^3$ is a bond of an oxirane ring;

$R^3$ is hydrogen or together to $R^2$ is a bond of an oxirane ring;

$R^4$ is hydrogen; methyl; $C_2$–$C_6$ alkyl or $C_3$–$C_6$ alkenyl or $C_2$–$C_6$ acyl, these alkyl, alkenyl and acyl groups being unsubstituted or substituted by a quaternary ammonium group or one or more $OR^7$, $NR^8R^9$, formyl, amidino, guanidinoimino or by $NR^8R^9$ and hydroxy;

$R^5$, $R^6$ are independently hydrogen; methyl; $C_2$–$C_6$ alkyl unsubstituted or substituted by one $NR^{10}R^{11}$, or $NR^{10}R^{11}$ and hydroxy, or $R^5$ and $R^6$ taken together with the nitrogen atom form an unsubstituted or substituted saturated or unsaturated penta- or hexa-monoheterocyclic ring, optionally containing another heteroatom chosen from oxygen or sulfur or nitrogen;

$R^7$ is hydrogen, methyl or $C_2$–$C_4$ alkyl, this alkyl being unsubstituted or substituted by one or more $NR^{10}R^{11}$ or by $NR^{10}R^{11}$ and hydroxy;

$R^8$, $R^9$ are independently hydrogen; methyl; $C_2$–$C_6$ alkyl or $C_3$–$C_6$ alkenyl, these alkyl and alkenyl groups being unsubstituted or substituted by one or more $NR^{10}R^{11}$, or $NR^{10}R^{11}$ and hydroxy, or $R^8$ and $R^9$ taken together with the nitrogen atom form an unsubstituted or substituted saturated or unsaturated penta- or hexa-monoheterocyclic ring, optionally containing another heteroatom chosen from oxygen or sulfur or nitrogen, or $R^8$ is hydrogen and $R^9$ is amidino;

$R^{10}$, $R^{11}$ are independently hydrogen, $C_1$–$C_6$ alkyl, or $R^{10}$ and $R^{11}$, taken together with the nitrogen atom form a saturated or unsaturated penta- or hexa-monoheterocyclic ring, including all of the possible stereoisomers, in particular Z and E isomers, optical isomers and their mixtures and the metabolites and the metabolic precursors of the compounds of formula (I).

2. A 17-(4-pyridazinyl)-5β,14β-androstane derivative of formula (I):

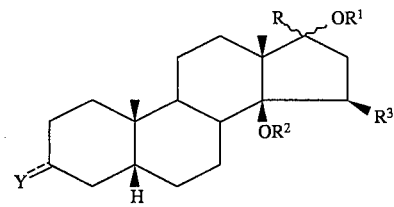

wherein:

the symbol ∼ means that the substituents in position 17 can have an α or β configuration;

the symbol --- represents a single or double bond;

Y is oxygen or guanidinoimino, when --- in position 3 is a double bond;

Y is hydroxy, $OR^4$ or $SR^4$, when --- in position 3 is a single bond and can have an α or β configuration;

R is an unsubstituted or substituted 4-pyridazinyl group;

$R^1$ is hydrogen; methyl; ethyl or n-propyl substituted by OH or $NR^5R^6$;

$R^2$ and $R^3$ form an oxirane ring;

$R^4$ is hydrogen; methyl; $C_2$–$C_6$ alkyl or $C_3$–$C_6$ alkenyl or $C_2$–$C_6$ acyl, these alkyl, alkenyl and acyl groups being unsubstituted or substituted by a quaternary ammonium group or one or more $OR^7$, $NR^8R^9$, formyl, amidino, guanidinoimino or by $NR^8R^9$ and hydroxy;

$R^5$, $R^6$ are independently hydrogen; methyl; $C_2$–$C_6$ alkyl unsubstituted or substituted by one $NR^{10}R^{11}$, or $NR^{10}R^{11}$ and hydroxy, or $R^5$ and $R^6$ taken together with the nitrogen atom form an unsubstituted or substituted saturated or unsaturated penta- or hexa-monoheterocyclic ring, optionally containing another heteroatom chosen from oxygen or sulfur or nitrogen;

$R^7$ is hydrogen, methyl or $C_2$–$C_4$ alkyl, this alkyl being unsubstituted or substituted by one or more $NR^{10}R^{11}$ or by $NR^{10}R^{11}$ and hydroxy;

$R^8$, $R^9$ are independently hydrogen; methyl; $C_2$–$C_6$ alkyl or $C_3$–$C_6$ alkenyl, these alkyl and alkenyl groups being unsubstituted or substituted by one or more $NR^{10}R^{11}$, or $NR^{10}R^{11}$ and hydroxy, or $R^8$ and $R^9$ taken together with the nitrogen atom form an unsubstituted or substituted saturated or unsaturated penta- or hexa-monoheterocyclic ring, optionally containing another heteroatom chosen from oxygen or sulfur or nitrogen, or $R^8$ is hydrogen and $R^9$ is amidino;

$R^{10}$, $R^{11}$ are independently hydrogen, $C_1$–$C_6$ alkyl, or $R^{10}$ and $R^{11}$, taken together with the nitrogen atom form a saturated or unsaturated penta- or hexa-monoheterocyclic ring, including all of the possible stereoisomers, in particular Z and E isomers, optical isomers and their mixtures and the metabolites and the metabolic precursors of the compounds of formula (I).

3. The 17-(4-pyridazinyl)-5β,14β-androstane derivative of claim 1, in the form of it's Z and E isomers, tautomers, optical isomers or mixtures thereof, metabolites or the metabolic precursors or pharmaceutically acceptable salts thereof.

4. A pharmaceutical composition comprising the 17-(4-pyridazinyl)-5β,14β-androstane derivative of claim 1, with a pharmaceutically acceptable carrier, diluent or a mixture thereof.

5. The 17-(4-pyridazinyl)-5β,14β-androstane derivative of claim 2, in the form of it's Z and E isomers, tautomers, optical isomers or mixtures thereof, metabolites or the metabolic precursors or pharmaceutically acceptable salts thereof.

6. A pharmaceutical composition comprising the 17-(4-pyridazinyl)-5β,14β-androstane derivative of claim 2, with a pharmaceutically acceptable carrier, diluent or a mixture thereof.

7. A compound, which is selected from:

3β-(2-Hydroxyethoxy)-17β-(4-pyridazinyl)-5β-androstane-14β,17α-diol,

3β-(3-Aminopropoxy)-17β-(4-pyridazinyl)-5β-androstane-14β,17α-diol,

3β-(2-(1-Pyrrolidinyl)ethoxy)-17β-(4-pyridazinyl)-5β-androstane-14β,17α-diol,

3β-(3-(1-Pyrrolidinyl)propoxy)-17β-(4-pyridazinyl)-5β-androstane-14β,17α-diol,

17β-(4-Pyridazinyl)-17α-(3-aminopropoxy)-5β-androstane-3β,14β-diol,

3β-(2-(1-Pyrrolidinyl)ethoxy)-17β-(4-pyridazinyl)-17α-methoxy-5β-androstan-14β-ol, 3β-(2-(1-Pyrrolidinyl)ethoxy)-17β-(4-pyridazinyl)-17α-(3-aminopropoxy)-5β-androstan-14β-ol, 14β,17α-Dihydroxy-17β-(4-pyridazinyl)-5β-androstan-3-one, 3-Guanidinoimino-17β-(4-pyridazinyl)-5β-androstane-14β,17α-diol, 14β,15β-Epoxy-17β-(4-pyridazinyl)-5β-androstane-3β,17α-diol, 17α-(4-Pyridazinyl)-5β-androstane-3β,14β,17β-triol, 3β-(2-(1-Pyrrolidinyl)ethoxy)-17α-(4-pyridazinyl)-5β-androstane-14β,17β-diol, 3β,17β-Bis(2-(1-pyrrolidinyl)ethoxy)-17α-(4-pyridazinyl)-5β-androstan-14β-ol, and the 3α derivatives of the above identified 3β derivatives and also the corresponding 3α and 3β thioderivatives (Y=S).

* * * * *